United States Patent [19]
Lindsey et al.

[11] Patent Number: 5,015,627
[45] Date of Patent: May 14, 1991

[54] STABILIZED SOMATOTROPIN FOR PARENTERAL ADMINISTRATION

[75] Inventors: Thomas O. Lindsey, Coatesville; Michael T. Clark, Downingtown, both of Pa.

[73] Assignee: SmithKline Beecham Corporation, Philadelphia, Pa.

[21] Appl. No.: 555,970

[22] Filed: Jul. 20, 1990

[51] Int. Cl.$^5$ .......................... A61K 37/02; C07K 7/10
[52] U.S. Cl. ............................................ 514/12; 514/2; 514/18; 514/21; 530/338; 530/345; 530/399
[58] Field of Search ............. 514/2, 18, 21, 12, 13–15; 530/338, 345, 399

[56] References Cited

U.S. PATENT DOCUMENTS

| | | | |
|---|---|---|---|
| 4,510,130 | 4/1985 | Platt et al. | 514/2 |
| 4,582,820 | 4/1986 | Teng | 514/2 |
| 4,866,040 | 9/1989 | Stracher et al. | 514/2 |
| 4,888,416 | 12/1989 | Janski et al. | 514/21 |

Primary Examiner—Lester L. Lee
Attorney, Agent, or Firm—William T. King; Stephen Venetianer; Edward T. Lentz

[57] ABSTRACT

A stabilized somatotropin peptide aldehyde complex which provides prolonged release of the somatotropin and enhanced feed efficiency. The complex is prepared by dissolving the somatotropin and peptide aldehyde in water, isolating the complex from the aqueous solution, and crystalizing the product from alcohol. Specifically, the complex comprises porcine somatotropin and leupeptin and is particularly useful for enhancing feed efficiency in swine.

10 Claims, No Drawings

STABILIZED SOMATOTROPIN FOR PARENTERAL ADMINISTRATION

FIELD OF THE INVENTION

This invention relates to a complex comprising a growth hormone and a peptide aldehyde. More specifically, this invention relates to a porcine somatotropin (PST)—leupeptin complex and to a method of producing stable PST compositions resulting in improved feed efficiency in the swine and a prolonged release of the PST.

BACKGROUND OF THE INVENTION

When porcine somatotropin is administered to pigs on a daily basis a marked improvement in feed efficiency, i.e., feed to gain, (the animal takes in less food and gains weight) and characteristic performances result. However, it is inconvenient to administer drugs to the swine on a daily basis because of the large expense and amount of time required to deliver the drug to each member of a large group of animals. It would, therefore, be more feasible to apply a single dose and have the PST release over a prolonged period of time. It would appear the easiest way to administer PST would be in a feed, however, like most proteins and macromolecular drugs, PST is not orally bioavailable. In general, the literature has not shown significant ability to deliver proteins and peptides via the oral route. The use of salicylates and mineral oil to enhance oral delivery of these drugs is disclosed in E.P. Application No. 0-177 342. U.S. Patent application 4,548,922, further discloses the use of steroid enhancers, such as fusidic acid.

Parenteral administration, for example, implants have been employed with other macromolecular drugs to give a prolonged release as disclosed in U.S. Pat. No. 4,666,704. PST is an unstable protein susceptible to enzymatic, as well as aqueous degradation. It reacts with itself and is readily cleaved by proteases. Indeed, the instability of the PST implant is thought to be due to the proteases that are generated at the implantation site because of the inflammatory response that takes place. It is because of this instability that the administration of PST to swine has hitherto been only marginally, if at all successful.

There is a commercial need for improved prolonged release implants for parenteral administration of macromolecular drugs having growth hormone activity.

It is, therefore, an object of this invention to provide a composition and method for stabilizing and releasing a biological active growth hormone in animals over a prolonged period of time.

It is a further object of this invention to provide a stable form of PST which will release in swine over a prolonged period of time and which results in improved bioavailability and feed efficiency.

DESCRIPTION OF INVENTION

In accordance with this invention, it has been discovered that when PST is reacted with leupeptin, a tripeptide aldehyde protease inhibitor, a complex is formed which is stable to proteolytic degradation, and has an increased biological half life and bioavailability. Further, this novel form of PST results in a very significant improvement in weight gain and feed-to-gain ratio for the animals. The new complex not only has the same bioactivity as PST, but also provides efficacy over a sustained period similar to daily injections of PST.

Many attempts were made to prepare a PST product which would overcome the above noted disadvantages and could be successfully administered to swine. For example, PST and leupeptin were mixed as dry powders, granulated and implants formed from the granulation. These implants were not efficacious and the administration to pigs at moderate levels for several days was detrimental to live performance.

Unexpectedly, it was discovered that when PST and leupeptin were dissolved in water and the complex was isolated from the solution, a crystalline product resulted which improved the feed efficiency of animals. The complex may be isolated from the aqueous solution by any method well known to the art, such as, for example, concentration, evaporation or lyophilization. Implants prepared from the complex and administered to pigs resulted in an improvement in daily weight gain and feed to-gain ratio.

The following formulations were prepared and compared for efficacy and stability.

| SDS2 | |
| --- | --- |
| Porcine Somatotropin | 99% |
| Leupeptin | 1% |

The above ingredients were mixed in a dry state and formed into 30 mg. pellets (implants) with a 3/16-inch punch and die and pressed to about 500 PSI.

| SDS4 | |
| --- | --- |
| Porcine Somatotropin | 99% |
| Leupeptin | 1% |

The PST and leupeptin were dissolved in water, and reacted at 39° C. for 6 hours. The water was slowly driven off and the resulting product was suspended in ethanol. The suspension was filtered and the precipitate dried overnight in a vacuum oven resulting in dried white crystals.

The crystalline complex was pelletized in the same manner as the dry mixture of SDS2.

A portion of the above pellets was spray coated with the following solution:

| | |
| --- | --- |
| Ethyl Cellulose | 40.0 g |
| Polyethylene Glycol | 10.0 g |
| Tween 80 | 1.0 g |
| Methylene Chloride | 1.0 L |

The ingredients were added to 600 ml. of methylene chloride and stirred at high speed until they were in solution. The volume was brought to 1.0L with methylene chloride.

The coating solution may be applied to the implants or pellets by any well known method to the art, such as, for example, by air suspension or pan coating. The sole purpose for coating the pellets is to eliminate the initial peak (dumping) of PST. This initial release of PST results in undesirable side effects which may be detrimental to the animal. The coating of the pellets does not contribute to the improved food efficiency or stability resulting from the novel PST—leupeptin complex of this invention.

The shape of the pellets or implants is not critical and any configuration suitable for implantation may be employed. In addition to the somatotropin and the leupeptin, it may be advantageous to include other pharmaceutical excipients in the compositions of this invention. For example, the implant may contain lubricants, such as, magnesium stearate or stearic acid, fillers, such as, sucrose or lactose and binders, such as, acacia, polyvinylpyrrolidone or gelatin.

The compositions of this invention may be administered to an animal parenterally employing any of the known implantation methods, such as subcutaneous, intramuscular and intraperitoneal. Preferably, the implant composition is subcutaneously implanted in an animal employing any well known technique.

Animals which are treated in this manner may include, without limitations, mammals such as cattle, sheep, goats, swine and the like, and birds such as poultry.

The following procedure was employed to determine plasma PST levels, feed consumption (average daily gain), and feed-to-gain.

Pigs were housed in an outdoor barn and acclimated 3-4 weeks to pens containing 7-8 pigs per pen. Within each pen pigs had access to a heated shelter and an ad libitum feed and water.

When most of the pigs reached approximately 75 kg, their weights were statistically compared and allotted to 6 different treatments, 3 pens per treatment, 3 pigs per pen (54 pigs total). The starting day was considered day 0, on which body weights, control blood samples and implants were initiated. When the pigs average body weights were approximately 77 Kg the study was initiated. At 107 Kg body weight the pigs were removed from the study, and if two pigs in a pen both weighed 107 Kg the third was also removed.

The pigs were injected with 1-2 coated pellets (depending on treatment) S.C. behind the ear. The Compudose implant gun was used and the site of administration was swabbed with 70% ETOH. The injection site was alternated left to right with each weekly injection. Pigs treated daily at 60 µg/kg were injected with a 1-½ 18 g needle in the neck area. Treatment was as follows:

(1) Control—Weekly—sham implant
(2) PST-Daily injection (60 µg/kg/day)
(3) PST-leupeptin implant-1 pellet @ 7 day interval (30 mg PST)
(4) PST-leupeptin implant-2 pellets @ 7 day interval (60 mg PST)
(5) PST-leupeptin implant-1 pellet @ 14 day interval (30 mg PST)
(6) PST-leupeptin implant-2 pellets @ 14 day interval (60 mg PST)

Blood samples were drawn from the snared pig via jugular vein, using a vacutainer with a 1-½ inch needle. The blood was allowed to clot, centrifuged and plasma removed. The plasma samples were frozen for PST determinations which were assayed at a later date.

FEED CONSUMPTION

All pigs received Enhanced Finisher diet #634 throughout the study. On day zero, two bags of feed were added to feeder and an initial weight taken. The feeders were checked daily and a bag of pre weighed feed was added as needed (feeders were never allowed to empty). A final weight of feeder was taken on the day all pigs were removed from a pen. The final weight was subtracted from initial weight and this was added to total feed added which equals Total Feed Consumption per pen.

Initial weight of feeder
− Final weight of feeder
Total
+ Total weight of bags of feed added
Total feed consumption per pen The pigs were weighed in kilograms individually on day zero and at seven day intervals throughout the study. Overall Average Daily Gain was derived by subtracting the initial weight on day zero from the pigs' final weight (pig removed from study) and dividing by number of days on study.

Feed-to-Gain per pen during the study was derived by adding all feed consumed per pen and dividing by total weight gain per pen.

The Average Daily Gain (ADG) and feed-to-gain results are presented in the following Table.

TABLE

| | Results from SDS 4 | | | |
|---|---|---|---|---|
| PST Treatments | Average Daily Gain, Kg | % of Control | Feed to Gain | % of Control |
| Control (no PST) | 0.82$^a$ | — | 3.77$^a$ | — |
| 60 µg/KG/d (5.2 mg/d) | 0.90$^{ab}$ | 9.7 | 2.59$^c$ | 31.2 |
| $_s$PST 30 mg @ 7d (4.3 mg/d) | 0.84$^a$ | 2.4 | 3.19$^{abc}$ | 15.3 |
| $_s$PST 60 mg @ 7d (8.6 mg/d) | 1.02$^b$ | 24.3 | 2.65$^c$ | 29.5 |
| $_s$PST 30 mg @ 14d (2.1 mg/d) | 0.86$^a$ | 4.9 | 3.45$^{ab}$ | 8.4 |
| $_s$PST 60 mg @ 14d (4.3 mg/d) | 0.87$^a$ | 6.1 | 3.09$^{bc}$ | 18.0 |

Within columns, means with differing superscripts are significantly different ($P < 0.5$).

The results of the plasma PST levels indicate that the daily injection of PST demonstrates very little, if any, plasma PST levels after 24 hours. In contrast, after injection of implants of the leupeptin—PST complex (SDS4) of this invention, a sustained plasma PST was noted for 8 to 10 days.

Further, the above results clearly indicate when the SDS4—PST leupeptin complex is administered to pigs by implantation, there is an increase over the control in both the average daily gain and feed-to-gain observed in the pigs.

In sharp contrast, when the PST and leupeptin were mixed in a dry state, Formula SDS2, and subjected to the same procedures, no increase in feed efficiency was noted. Indeed, all the results demonstrated a lower daily weight gain and feed to-gain ratio than the control. None of the SDS2 drug mixtures proved to be efficacious. Further, the administration of this formulation over several days was detrimental to the live performance of the pig.

The leupeptin may be present in the complex from about .05% to about 10% by weight. Preferably, the leupeptin may be present from about 0.5% to about 5.0% by weight. Exemplary of other peptide aldehydes beside leupeptin that may be employed in this invention are elastinal, chymostatin and antipain.

In a preferred embodiment the compositions and method of this invention are applicable to animal growth hormones, such as, for example, humans, bovine, avian, porcine, equine or ovine. Most advantageously, the compositions and method are applicable to porcine somatotropin.

The method in accordance with this invention comprises parenterally administering to an animal organism the above PST—leupeptin complex in an amount sufficient to enhance weight gain and feed efficiency. The dose is dependent on several factors, for example, the size of the animal and the effect desired. For administration to swine, the complex, preferably, will be in an amount of from 10 mg. to about 500 mg., advantageously from about 30 mg. to about 75 mg. Equal doses will be administered at intervals of about 7 to 42 days, preferably, every 10 days.

What is claimed is:

1. A method for improving feed efficiency in animals which comprises parenterally administering to an animal organism in an amount sufficient to produce said efficiency a growth promoting agent being a complex of a porcine somatotropin and from about .05% to about 10% of a peptide aldehyde selected from the group consisting of leupeptin, elastinal, chymostatin and antipain.

2. The method of claim 1 in which the peptide aldehyde is leupeptin and the somatotropin is porcine somatotropin.

3. The method of claim 1 in which the complex is administered in an amount of from about 10 mg to about 500 mg.

4. The method of claim 5 in which the administration is done at from about 7 to 42 day intervals.

5. The method of claim 1 in which the complex is administered subcutaneously as an implant.

6. A method for preparing a stable somatotropin complex having a prolonged release of the somatotropin which comprises dissolving the somatotropin and a peptide aldehyde in water, isolating the complex from the aqueous solution, and crystalizing the complex from alcohol.

7. The method of claim 8 in which the alcohol is ethanol.

8. The method of claim 8 in which the somatotropin is porcine somatotropin and the peptide aldehyde is leupeptin.

9. A complex for improving feed efficiency and obtaining a prolonged release of a somatotropin which comprises porcine somatotropin and leupeptin.

10. A complex for improving feed efficiency and obtaining a prolonged release of a somatotropin which comprises a somatotropin selected from the group consisting of porcine, bovine, avian, equine and ovine and from about .05% to about 10% of a peptide aldehyde selected from the group consisting of leupeptin, elastinal chymostatin and antipain.

* * * * *